(12) United States Patent
Profio et al.

(10) Patent No.: US 10,265,044 B2
(45) Date of Patent: Apr. 23, 2019

(54) SYSTEMS AND METHODS FOR ADAPTIVE IMAGING SYSTEMS

(71) Applicant: General Electric Company, Schenectady, NY (US)

(72) Inventors: Mark Vincent Profio, Waukesha, WI (US); John Londt, Oconomowoc, WI (US); Darin Okerlund, Waukesha, WI (US); John Irvin Jackson, Brookfield, WI (US)

(73) Assignee: General Electric Company, Schenectady, NY (US)

( * ) Notice: Subject to any disclaimer, the term of this patent is extended or adjusted under 35 U.S.C. 154(b) by 77 days.

(21) Appl. No.: 15/253,276

(22) Filed: Aug. 31, 2016

(65) Prior Publication Data
US 2018/0061045 A1    Mar. 1, 2018

(51) Int. Cl.
| G06K 9/00 | (2006.01) |
| A61B 8/00 | (2006.01) |
| G06T 11/00 | (2006.01) |
| A61B 6/03 | (2006.01) |
| A61B 6/00 | (2006.01) |
| G06F 19/00 | (2018.01) |
| G06T 7/00 | (2017.01) |

(52) U.S. Cl.
CPC .............. *A61B 8/00* (2013.01); *A61B 6/032* (2013.01); *A61B 6/037* (2013.01); *A61B 6/58* (2013.01); *G06F 19/00* (2013.01); *G06T 7/0002* (2013.01); *G06T 11/008* (2013.01); *A61B 8/54* (2013.01); *G06T 2207/10072* (2013.01); *G06T 2207/30168* (2013.01)

(58) Field of Classification Search
CPC ....... G06T 7/0012; G06T 5/00; G06T 11/008; G06T 11/003; A61B 6/032
USPC ........................................................ 382/131
See application file for complete search history.

(56) References Cited

U.S. PATENT DOCUMENTS

| 4,835,690 A | 5/1989 | Gangarosa et al. |
| 7,529,394 B2 | 5/2009 | Krishnan et al. |
| 7,949,167 B2 | 5/2011 | Krishnan et al. |

(Continued)

FOREIGN PATENT DOCUMENTS

| CA | 2577652 A1 | 11/2015 |
| WO | 2015109388 A1 | 7/2015 |

*Primary Examiner* — Van D Huynh
(74) *Attorney, Agent, or Firm* — Dean D. Small; The Small Patent Law Group, LLC

(57) ABSTRACT

A system includes an imaging acquisition unit, a reconstruction unit, and a determination system. The imaging acquisition unit is configured to perform a scan to acquire imaging information of a patient. The reconstruction unit is configured to reconstruct an image using the imaging information. The determination system is communicatively coupled to the imaging acquisition unit and the reconstruction unit. The determination system includes at least one processor configured to: acquire performance information corresponding to the scan; determine a scan quality for the scan based on the performance information; determine an update to a protocol used to at least one of acquire the imaging information or reconstruct the image; and provide control information to at least one of the imaging acquisition unit or the reconstruction unit to implement the determined update for at least one of performing a subsequent scan or reconstructing a subsequent image.

20 Claims, 4 Drawing Sheets

(56) References Cited

U.S. PATENT DOCUMENTS

| | | | |
|---|---|---|---|
| 2006/0112033 A1 | 5/2006 | Vion et al. | |
| 2014/0029818 A1* | 1/2014 | McCoy | G06F 19/321 |
| | | | 382/131 |
| 2014/0161335 A1* | 6/2014 | Song | A61B 6/585 |
| | | | 382/131 |
| 2015/0201895 A1 | 7/2015 | Suzuki | |
| 2016/0078619 A1* | 3/2016 | Hsieh | A61B 6/032 |
| | | | 378/4 |
| 2017/0238882 A1* | 8/2017 | Ma | A61B 6/032 |

* cited by examiner

SYSTEMS AND METHODS FOR ADAPTIVE IMAGING SYSTEMS

BACKGROUND OF THE INVENTION

The subject matter disclosed herein relates generally to systems and methods for imaging (e.g., diagnostic imaging of a patient).

In CT imaging, for example, an X-ray source may be rotated around an object of interest (e.g., a patient, organ of a patient) to obtain imaging information. During a clinical scan, X-rays emitted from the X-ray source, attenuated by the object of interest, may be collected or detected by a detector and used to reconstruct a medical image. Various settings may be used to control the performance of equipment to acquire CT imaging information as well to reconstruct images using acquired information. However, selecting effective combinations of settings of different parameters is difficult, and it is difficult, with conventional imaging systems, to evaluate whether the selection of parameters is properly optimizing the imaging process.

BRIEF DESCRIPTION OF THE INVENTION

In one embodiment, a system is provided that includes an imaging acquisition unit, a reconstruction unit, and a determination system. The imaging acquisition unit is configured to perform a scan to acquire imaging information of a patient. The reconstruction unit is configured to reconstruct an image using the imaging information. The determination system is communicatively coupled to the imaging acquisition unit and the reconstruction unit. The determination system includes at least one processor configured to: acquire performance information corresponding to the scan; determine a scan quality for the scan based on the performance information; determine an update to a protocol used to at least one of acquire the imaging information or reconstruct the image; and provide control information to at least one of the imaging acquisition unit or the reconstruction unit to implement the determined update for at least one of performing a subsequent scan or reconstructing a subsequent image.

In another embodiment, a method is provided. The method includes acquiring imaging information of a patient via with an imaging acquisition unit. The method also includes reconstructing, with a reconstruction unit, an image using the imaging information. Also, the method includes determining, with at least one processor, performance information corresponding to the scan. Further, the method includes determining, with the at least one processor, a scan quality for the scan based on the performance information. The method also includes determining, with the at least one processor, an update to a protocol used to at least one of acquire the imaging information or reconstruct the image; and providing control information to at least one of the imaging acquisition unit or the reconstruction unit to implement the determined update for at least one of performing a subsequent scan or reconstructing a subsequent image.

In another embodiment, a tangible and non-transitory computer readable medium is provided. The tangible and non-transitory computer readable medium includes one or more computer software modules configured to direct one or more processors. The tangible and non-transitory computer readable medium is configured to direct the one or more processors to: determine performance information corresponding to a scan; determine a scan quality for the scan based on the performance information; determine an update to a protocol used to perform the scan; and provide control information to at least one of an imaging acquisition unit or a reconstruction unit to implement the determined update for at least one of performing a subsequent scan or reconstructing a subsequent image.

DETAILED DESCRIPTION OF THE INVENTION

Figure 1:
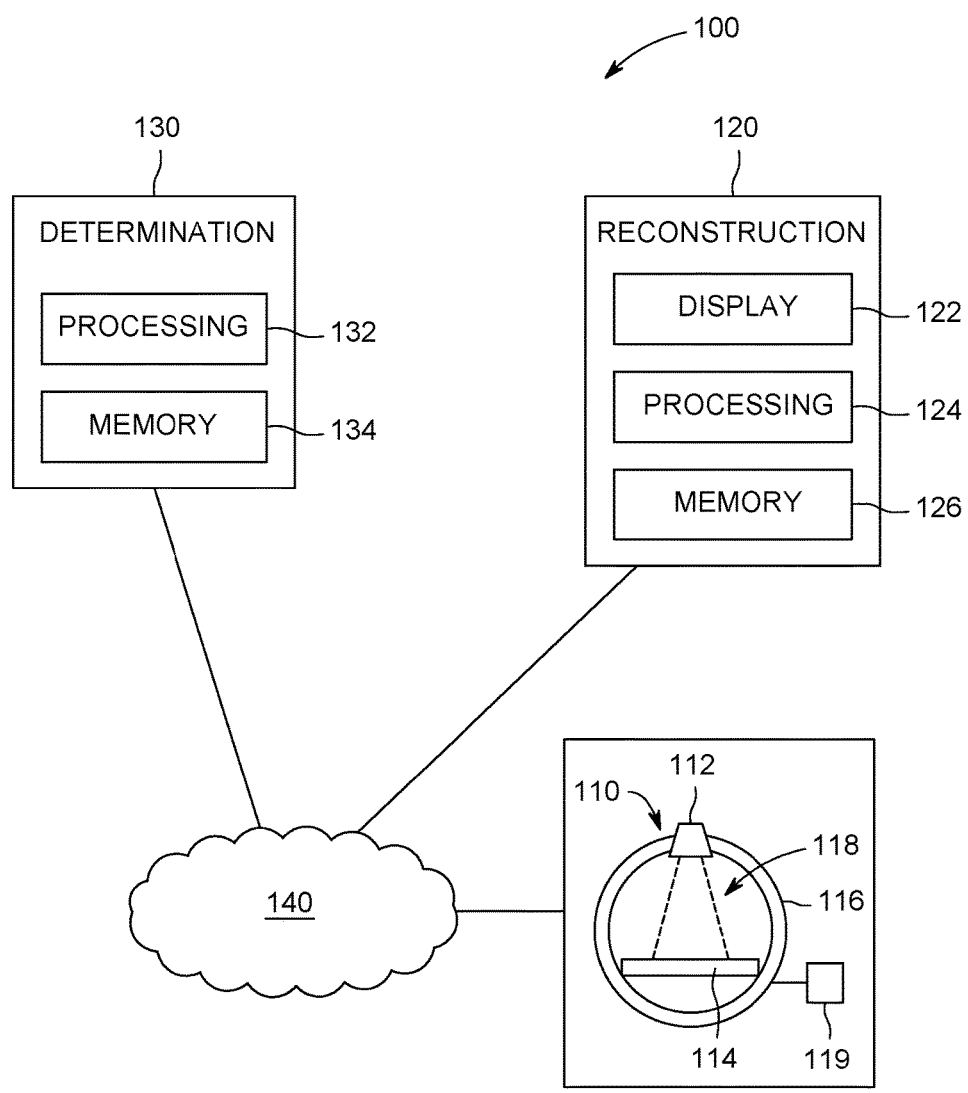
FIG. 1 is a schematic block diagram illustrating a system in accordance with various embodiments described herein.

The following detailed description of certain embodiments will be better understood when read in conjunction with the appended drawings. To the extent that the figures illustrate diagrams of the functional blocks of various embodiments, the functional blocks are not necessarily indicative of the division between hardware circuitry. For example, one or more of the functional blocks (e.g., processors or memories) may be implemented in a single piece of hardware (e.g., a general purpose signal processor or a block of random access memory, hard disk, or the like) or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings.

As used herein, the terms "system," "unit," or "module" may include a hardware and/or software system that operates to perform one or more functions. For example, a module, unit, or system may include a computer processor, controller, or other logic-based device that performs operations based on instructions stored on a tangible and non-transitory computer readable storage medium, such as a computer memory. Alternatively, a module, unit, or system may include a hard-wired device that performs operations based on hard-wired logic of the device. Various modules or units shown in the attached figures may represent the hardware that operates based on software or hardwired instructions, the software that directs hardware to perform the operations, or a combination thereof.

"Systems," "units," or "modules" may include or represent hardware and associated instructions (e.g., software stored on a tangible and non-transitory computer readable storage medium, such as a computer hard drive, ROM, RAM, or the like) that perform one or more operations described herein. The hardware may include electronic circuits that include and/or are connected to one or more logic-based devices, such as microprocessors, processors, controllers, or the like. These devices may be off-the-shelf devices that are appropriately programmed or instructed to perform operations described herein from the instructions described above. Additionally or alternatively, one or more of these devices may be hard-wired with logic circuits to perform these operations.

As used herein, an element or step recited in the singular and preceded with the word "a" or "an" should be understood as not excluding plural of said elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional elements not having that property.

Various embodiments provide systems and methods for adaptively adjusting, modifying, or otherwise updating protocols used to acquire imaging information and/or reconstruct images. Various embodiments provide for the gathering and production of data for measuring acquisition and/or reconstruction performance to improve diagnostic success rates. Various embodiments utilize user assessments or user feedback to measure or analyze acquisition and/or reconstruction performance. Images for specific clinical tasks may be examined on a clinical task basis to determine combinations of settings used for successful outcomes for each particular clinical task. In various embodiments, automated image quality (IQ) metrics and/or user feedback are utilized to measure critical to quality factors (CTQ) being optimized by clinical intent or task. Various embodiments provide for clinical task driven, automated performance quantification with user feedback for optimizing imaging acquisition and image reconstruction.

Various embodiments provide systems and methods for evolving and optimizing scanning performance for many user personas and patient demographics. Improvements to protocols, assist features, and/or profiles may be determined via a comparative study of protocols used (e.g., values of scanning and/or reconstruction parameters used) to acquire previous images. The determined improvements may be suggested to a user and/or automatically implemented. Various embodiments provide for the use of evaluative feedback of protocols based on determined image quality to provide closed loop adjustment of scanning and/or reconstruction settings.

A technical effect of various embodiments described herein includes improving scanner automation and clinical utility of scanning equipment. A technical effect of various embodiments described herein includes improved image quality. A technical effect of various embodiments described herein includes improved diagnostic capability.

FIG. 1 illustrates a system 100 formed in accordance with various embodiments. As seen in FIG. 1, the system 100 includes an imaging acquisition unit 110, a reconstruction unit 120, a determination system 130, and a link 140. Generally, the imaging acquisition unit is configured to perform a scan to acquire imaging information. The reconstruction unit 120 is configured to reconstruct an image using the imaging information acquired by the imaging acquisition unit 110. The determination system 130 is communicatively coupled to the imaging acquisition unit 110 and the reconstruction unit 120 (e.g., via the link 140), and is configured to acquire imaging performance information corresponding to the image, determine a scan quality for the scan based on the imaging performance information, determine an update to a protocol used to at least one of acquire the imaging information or reconstruct the image, and provide control information to at least one of the imaging acquisition unit 110 or the reconstruction unit 120 to implement the determined update for at least one of performing a subsequent scan or reconstructing a subsequent image. The link 140 may include wired or wireless connections. Further, the depicted link 140 may also represent additional processors or processing systems. For example, the link 140 may provide internet connectivity and include web-based processing (e.g., using remote servers and/or processors). In some embodiments, the link 140 includes cloud based computing capabilities. It may be noted that various aspects of the system 100 may be located in a common room or facility, or may be located remotely from one or more aspects of the system 100. For example, each of the imaging acquisition unit 110, reconstruction unit 120, and determination system 130 may be located remotely from each other. Further, each of the imaging acquisition unit 110, reconstruction unit 120, and determination system 130 may utilize processing (e.g., via remotely located processing units) associated with or provided by the link 140.

The depicted imaging acquisition unit 110 is configured to acquire imaging information of a patient. In various embodiments, the imaging acquisition unit 110 may be configured to acquire imaging information using, by way of example, one or more of computed tomography (CT), positron emission tomography (PET), single photon emission tomography (SPECT), or ultrasound (US), among others. In the illustrated example, the imaging acquisition unit is configured to collect imaging information using CT. The depicted example acquisition unit 110 is configured as a CT acquisition unit, and includes an X-ray source 112 and a CT detector 114. (For additional information regarding example CT systems, see FIG. 4 and related discussion herein.) The X-ray source 112 and the CT detector 114 (along with associated components such as bowtie filters, source collimators, detector collimators, or the like (not shown in FIG. 1)) may rotate about a central axis of a bore 118 of a gantry 116 of the acquisition unit 110.

Generally, X-rays from the X-ray source 112 may be guided to an object to be imaged through a source collimator and bowtie filter. The object to be imaged, for example, may be a human patient or a portion thereof (e.g., head or torso, among others). The source collimator may be configured to allow X-rays within a desired field of view (FOV) to pass through to the object to be imaged while blocking other X-rays, for example to define a slab width or extent along a z-axis (an axis extending along the length of the bore 118) of the patient to be imaged. The bowtie filter may be configured to absorb radiation from the X-ray source 112 to control distribution of X-rays passed to the object to be imaged.

X-rays that pass through the object (e.g., human patient or portion thereof) to be imaged are attenuated by the object and received by the CT detector 114 (which may have a detector collimator associated therewith), which detects the attenuated X-rays and provides imaging information to the reconstruction unit 120 and/or determination system 130. For example, the reconstruction unit 130 may then reconstruct an image of the scanned portion of the object using the imaging information (or projection information) provided by the CT detector 114. It may be noted that the acquisition unit 110 may also include a reconstruction unit (not shown in FIG. 1) configured to provide an image for viewing by an operator of the acquisition unit 110. The acquisition unit 110 includes an input unit 119 that is configured to obtain input corresponding to a scan to be performed, with a processing unit (not shown in FIG. 1) of the acquisition unit 110 configured to use the input to determine one or more scan settings (e.g., tube voltage, tube current, scanning rotation speed, or the like). For example, the input unit 119 may receive information from an operator to determine a protocol to be used, with the protocol setting forth tube voltage, tube current, collimation width, scanning rotation speed, or the like. The protocol may be specified or updated by the determination unit 130 as discussed herein. Further, additional information may be obtained during a scan to tailor the scan settings for the particular scan. For example, for certain types of scans, the heart rate may be determined and used to tailor one or more scanning parameters. The input unit 119 may include a keyboard, mouse, touchscreen or the like to receive input from an operator, and/or may include a port or other connectivity device to receive input from a computer or other source such as the determination unit 130, and/or may include a sensor attached to a patient. The input unit 119 may also include a display configured to provide assist features to an operator during set-up and/or performance of a scan.

In the illustrated embodiment, the X-ray source 112 is configured to rotate about the object. For example, the X-ray source 112 and the CT detector 114 may be positioned about a bore 118 of the gantry 116 and rotated about the object to be imaged. As the X-ray source 112 rotates about the object during an imaging scan, X-rays received by the CT detector 114 during one complete rotation provide a 360 degree view of X-rays that have passed through the object. Other imaging scanning ranges may be used in alternative embodiments. The scanning range (or ranges) may be specified by a protocol. The CT imaging information may be collected as a series of views that together make up a rotation or portion thereof. A blanking interval for may separate a first view or projection from the next view or projection in the series.

As discussed herein, the acquisition unit 110 may follow one or more scanning protocols to perform a scan. It may be noted that a protocol as discussed herein may include one or both of scanning parameters (values of parameters used to acquire imaging information as part of a scanning protocol or scanning portion of a protocol) or reconstruction parameters (values of parameters used to reconstruct an image as part of a reconstruction protocol or reconstruction portion of a protocol). In various embodiments, the protocol used for a scan corresponds to the clinical task to be performed with the scan. For example, each clinical task may have a protocol specifying scanning acquisition parameter values to be used for that particular clinical task. A clinical task, for example, may correspond to a portion of the body to be imaged and/or a purpose of the scan. A clinical task may be defined by a clinical identifier (CID). Examples of clinical tasks include analysis of a tumor, analysis of a metal implant in a joint, cardiac CTA, neurological perfusion analysis, liver lesion analysis, chest examination, COW/carotid analysis, abdomen examination, or pelvic examination, among others. Additional discussion regarding CIDs and selection of protocols and/or profiles may be found in U.S. patent application Ser. No. 14/788,033, "Systems and Methods for Flow Rate Compensated Acquisition Parameters for Medical Imaging," filed Jun. 30, 2015, the subject matter of which is hereby incorporated by reference in its entirety.

It may be noted that a given protocol may also include profiles and/or assist features configured to tailor performance of the protocol for a particular patient. For example, in various embodiments, a scan protocol includes a clinical context flag or CID. The CID provides a clinical context for which multiple solutions (where solutions are understood as collections or combinations of parameter settings) are possible. As discussed herein, the determination system 130 uses the clinical context, patient attributes, prior imaging example results, patient history information, and/or likely findings associated with the clinical context to determine the best solution. For instance, in a clinical context for which in-plane motion is a concern, solutions that used slower gantry speeds would be avoided. Further, for each clinical task or context, critical to quality factors (CTQ's) may be defined. The CTQ's may be used to control assist features, which may be used to select appropriate scan (and/or reconstruction) parameters. By way of example and not limitation, the below chart lists example clinical tasks, along with corresponding primary and secondary CTQ's, as well as degrees of freedom (e.g., operation aspects for which control parameters or settings may be varied to help satisfy the CTQ's or other performance targets for a given scan). It may be noted that resolution may be understood as a CTQ as well as a degree of freedom. For example, resolution may be adjusted by adjusting a related scan parameter (e.g., focal spot size for spatial resolution, gantry rotational speed for temporal resolution). It may be noted that other clinical tasks, primary CTQ's, secondary CTQ's, and degrees of freedom may be utilized in alternate embodiments.

| Clinical Task | Primary CTQ's | Secondary CTQ's | Degrees of Freedom |
|---|---|---|---|
| Cardiac CTA | Spatial resolution, Temporal resolution | Noise | Gantry speed (rotational speed), Focal spot size, Dose |
| Dynamic Neurological Perfusion | Time to diagnosis, contrast sampling, Low contrast detectability (LCD), Perfusion map accuracy | | Temporal resolution (e.g., rotational speed, helical pitch, table speed), Dose |
| Liver Lesion | Contrast, LCD, Material density (MD) accuracy | | Spatial resolution (e.g., focal spot size), Temporal resolution |
| PE, Chest | Temporal resolution, Contrast, Spatial resolution | MD accuracy, Coverage | Spatial resolution (e.g., focal spot size), Temporal resolution (e.g., rotational speed, helical pitch, table speed) |
| COW/Carotid | Spatial resolution, Contrast | MD accuracy | Temporal resolution |
| Routine Abdomen/Pelvis | Dose, General Image Quality (IQ) | Spatial resolution, MD accuracy | Temporal resolution |

As discussed herein, the CID may also be logically mapped to an Assist Profile or assist feature (which may be understood as a sub-protocol or as part of an overall protocol). In various embodiments, the assist profile corresponds to clinically relevant prioritization of imaging CTQ's for a given scan for a given patient. MD accuracy, contrast to noise ratio (CNR), spatial resolution, temporal resolution, and coverage are examples of CTQ's that may be prioritized pursuant to an assist feature. It may be noted that scanning techniques such as single or dual energy CT, Cardiac CT, or contrast management may be addressed with an assist feature. The above techniques are provided by way of example, and other techniques may additionally or alternatively addressed with an assist feature, with profiles developed for one or more specific aspects of a given scan or patient examination.

Given the clinical task as well as patient information (which may include manually entered information and/or sensed or obtained information, such as a scout scan), a final set of acquisition and/or reconstruction parameters may be selected, for example, based on one or more of an IQ metric (e.g., noise index), dose target, patient size (e.g., as determined from scout scan), prior images, prior findings, patient medical history, or actual patient coverage in the z-direction. By way of example and not limitation, the below chart lists example assist features, along with corresponding goals and CTQ's, as well as degrees of freedom (e.g., operation aspects for which control parameters or settings may be varied to help satisfy the CTQ's or other performance targets for a given scan). It may be noted that other assist features, goals, CTQ's and/or degrees of freedom may be utilized in alternate embodiments.

| Assist Feature | Goal | CTQ's | Degrees of Freedom |
|---|---|---|---|
| Gating, arrhythmia management, CCTA | Automate, prescribe, acquire, and reconstruct the phases of least motion for CCTA patient and correct remaining temporal motion | Minimizing cardiac motion | Cardiac scanning and reconstruction parameters |
| Automatic Exposure Control | Select appropriate tube current (mA) for clinical task | Noise target, patient size adjustment, dose | Tube current (mA) |
| kV Assist | Select appropriate tube voltage (kV) for clinical task | CNR, maximum allowable noise, patient size adjustment, dose | Tube voltage (kV) |
| Contrast Management | Assist setup and monitoring contrast injections (e.g., to obtain appropriate contrast levels for clinical task) | Contrast uniformity, Contrast level, Minimization of contrast dose | Contrast injection parameters, scan speed (pitch, collimation, etc.) |
| Dual energy | Select acquisition and reconstruction parameters appropriate for specific clinical use cases | MD accuracy, Spatial resolution, Temporal resolution, Artifact control, LCD, Contrast, Z coverage | Field of view (SFOV), Bowtie filter settings, Collimation, Rotational speed, Helical Pitch, voltage (keV) |

Accordingly, assist features and/or associated profiles in various embodiments provide a set of possible solutions for a given scan. For example, assist features and/or associated profiles may include preset families of settings for dual energy CT that include acceptable acquisition parameters. Additionally, assist features and/or associated profiles may include clinically relevant reconstruction settings, contrast timing parameters, and/or cardiac acquisition phases, among others.

Generally, a protocol may set acquisition and/or reconstruction parameter settings which may be supplemented and/or modified using assist features to tailor a scan for a given particular situation (e.g., based on individual patient characteristics). The protocol may specify which additional information to use in conjunction with an assist feature and/or how to use the additional information (e.g., how to adjust one or more scanning parameters based on additional information acquired with an assist feature).

The depicted reconstruction unit 120 is configured to reconstruct one or more images using the imaging information acquired by the imaging acquisition unit 110. It may be noted that more than one reconstruction unit 120 may be employed in various embodiments. For example, the acquisition unit 110 may have a reconstruction unit 120 integrated therein or associated therewith, for example, to allow an operator of the imaging acquisition unit 110 to review one or more images to confirm if the scan is acceptable or if the scan should be re-performed. One or more reconstruction units 120 may be located remotely from the acquisition unit.

Generally, the reconstruction unit 120 receives imaging information from the imaging acquisition unit 110, and uses the imaging information to reconstruct an image, which may be then reviewed by a user using the reconstruction unit 120 and/or communicated to a user located remotely from the reconstruction unit 120.

In various embodiments, a viewer of an image generated by the reconstruction unit 120 may provide comments or ratings regarding the quality and/or usefulness of the image. For example, a user may be prompted to provide a rating or comment. In the illustrated embodiment, the reconstruction unit 120 includes a display 122, a processing unit 124, and a memory 126. The reconstruction unit 120 in various embodiments is configured to prompt a user via the display 122 to provide a qualitative user input information. The qualitative user input information, for example, may be used by the determination unit as all or a part of the imaging performance information used to determine the scan quality and determine an update to a protocol.

As discussed herein, a protocol may include reconstruction parameter settings. In some embodiments, an image based CID may be specified and associated with one or more reconstruction image sets and/or acquiring imaging information to be reconstructed. The image CID may be used to notify a server, workstation, cloud arrangement, or other processing system to begin an automated application based pre-processing, for example pre-processing in a background as soon as images or imaging information is received. As discussed herein, automated image-based metrics may be generated to quantify or describe the CTQ performance based on the reconstructed images. The automated image-based metrics may be generated using images provided by the reconstruction unit 120.

The depicted determination system 130 is communicatively coupled (e.g., via link 140) to the imaging acquisition unit 110 and the reconstruction unit 120. The determination system 130 includes at least one processor (e.g., processing unit 132) and is configured to acquire performance information corresponding to a scan performed using the system 100. For example, the performance information may correspond to usage information (e.g., settings used to acquire scanning information and/or reconstruct an image). As another example, the performance information may additionally or alternatively include imaging performance information corresponding to an image reconstructed by the reconstruction unit 120 using imaging information acquired by the imaging acquisition unit 110. The determination system 130 of the illustrated example is also configured to determine a scan quality for the scan based on the imaging performance information, to determine an update to a protocol used to at least one of acquire the imaging information or reconstruct the image, and to provide control information to at least one of the imaging acquisition unit 110 or the reconstruction unit 120 for at least one of performing a subsequent scan or reconstructing a subsequent image.

The determination system 130, for example, acquires imaging performance information corresponding to the image reconstructed by the reconstruction unit 120. For example, the imaging performance information may be acquired from the imaging acquisition unit 110 and/or a user associated therewith (e.g., a measured performance such as time to acquire scan, and/or a user provided rating or comment provided by an operator of the imaging acquisition unit 110). As another example, the imaging performance information may be additionally or alternatively acquired from the reconstruction unit 120 and/or a user associated therewith. For example, an automated image performance metric may be determined by one or more of the determination system 130, reconstruction unit 120, or other processor (e.g., associated with or coupled to the determination system 130 via the link 140). Automated image performance metrics may be used to automatically quantify, for example, image-based IQ metrics (e.g., noise, resolution, SNR), scan success, contrast timing, acquisition timing, or dose vs. IQ. Additionally or alternatively, a viewer analyzing the image may provide a rating and/or comment that constitutes all or a portion of the imaging performance information. The determination system 130 may then determine a scan quality for the scan based on the imaging performance information. The scan quality may be expressed quantitatively (e.g., a numerical rating such as a percentage of a maximum score) or qualitatively (e.g., acceptable or unacceptable, or part of a range such as very good, good, average, poor). The imaging performance information may include an automatically determined image quality metric and/or qualitative user input information as discussed herein, with the scan quality determined using the automatically determined image quality metric and/or qualitative user input information.

As discussed herein, automated performance metrics may be generated to measure CTQ performance for specific clinical tasks and/or assist features. By way of example and not limitation, example metrics include X-ray dose, contrast media load, contrast to noise ratio (CNR), image noise, image texture, material density accuracy, phases acquired, contrast opacification, artifact measures, iodine contamination, resulting image motion or temporal resolution, spatial resolution, coverage time, reconstruction transfer times, network transfer times, or low contrast detectability. One or more of the above listed (and/or other) metrics may be used to evaluate a given scan, and to help determine if an adjustment to a protocol should be made to improve performance. Additionally or alternatively, user ratings based on a user's evaluation of one or more images may be used to evaluate a scan and/or determine if an adjustment to a protocol should be made to improve performance. By way of example and not limitation, the below chart lists example clinical tasks, assist features, and associated CTQ performance metrics or considerations. It may be noted that other clinical tasks, assist features, and/or CTQ performance metrics may be utilized in alternate embodiments.

| Clinical Task | Assist Feature | CTQ Performance Metrics |
| --- | --- | --- |
| Cardiac CTA | Autogating, arrythmia management, kV assist, mA assist | Were the required phases acquired? Do the resulting images have residual motion? Were the desired contrast opacification and uniformity achieved? What is the noise/CNR of the resulting image? |
| Dynamic Neurological Perfusion | Prioritized reconstruction, prioritized, networking reconstruction flow optimization | How fast were the images reconstructed? How long before the images were post-processed? What was the noise/CNR of the resulting image? What was the temporal sampling vs. contrast of the output image(s)? How well registered was the image volume? |
| Liver Lesion | Dual energy assist, mA assist, kV assist, contrast assist | What were the dose and image quality (IQ) metrics attained? What was the image noixe/CNR of the resulting image(s)? What was the Iodine contamination in Ca images? What was the image texture in keV images? |

As discussed herein, user ratings may be used additionally or alternatively to automated metrics to evaluate performance of a scan (e.g., compare results of a scan to previous scans, and determine if an adjustment to protocol may be made to improve performance based on the comparison). In various embodiments, user (e.g., operators and/or clinicians) feedback may be utilized. For example, a contextual comment-providing application with individual user login profiles may be utilized. Additionally or alternatively, users may provide feedback on their assessment of the clinical task CTQ's performance. User ratings may be used to confirm, supplement, and/or replace automated metrics, for example to customize modification of a given protocol for preferences of a given user or group of users. Accordingly, user ratings may be used to inform data analytics algorithms to better optimize protocols profiles in combination with data oriented metrics. It may be noted that automated metrics and/or user ratings may include one or more figures of merit. (See, e.g., FIG. 3 and related discussion.) As part of a closed loop system, protocols, assist features, and profiles may be improved to improve clinical outcomes. In various embodiments, user ratings may be provided via a mobile device used by a user of the acquisition unit and/or reconstruction unit. It may be noted that user comments may be used to evaluate performance, as well as to determine if metrics for a given scan should be considered, or altered based on a user experience. For example, if a user provides a note that excessive patient motion was present during a scan, poor image quality may be attributed to the motion and not attributed to the particular protocol employed.

The depicted determination system 130 also determines an update to a protocol used to at least one of acquire the imaging information or reconstruct the image. The update to the protocol may include an update to an assist feature and/or profile as discussed herein, and/or to an algorithm utilized by the assist feature and/or profile. Generally, the update may be determined based on the scan quality and historical information. For example, the scan quality for a given scan may be compared to historical results for previous scans for similar clinical contexts, with the scan protocol for the given scan also compared to corresponding scan protocols used to obtain the historical results. If, for example, the current scan quality is lower than historical scan qualities, the corresponding protocols may be analyzed (e.g., automatically by the determination unit) to determine differences between the currently studied protocol and past protocols associated with more successful scans or better scan qualities, and to determine one or more potential updates to the currently studied protocol to improve performance based on the determined differences.

The depicted determination system 130 is also configured to provide control information to at least one of the imaging acquisition unit 110 or the reconstruction unit 120 to implement the determined update to the protocol for at least one of performing a subsequent scan or reconstructing a subsequent image. For example, the determination system 130 may provide control information to the imaging acquisition unit 110 to update a scanning parameter used to acquire imaging information. As another example, the determination system 130 may provide control information to the reconstruction unit 120 to update a reconstruction parameter used to reconstruct an image using acquired imaging information.

In some embodiments, the control information includes a user prompt corresponding to an update of the protocol. For example, a user of the imaging acquisition unit 110 may be provided with a prompt describing a change in protocol to acquire imaging information. The user may then approve, decline, or modify the change in protocol. Additionally or alternatively, a user of the reconstruction unit 120 may be provided with a prompt describing a change in protocol to reconstruct an image. Again, the user may then approve, decline, or modify the change in protocol. In some embodiments, the control information includes an automatic update of the protocol. Accordingly, the protocol for a given clinical context may be updated autonomously (without user intervention) in various embodiments.

As discussed herein, in some embodiments the control information adjusts scanning parameters for acquiring imaging information. For example, one or more of a tube voltage (or technique or algorithm for determining tube voltage), tube current (or technique or algorithm for determining tube current), focal spot size (or technique or algorithm for determining focal spot size), collimation width (or technique or algorithm for determining collimation width), or rotational speed of a gantry (or technique or algorithm for determining rotational speed) may be adjusted. Additional examples of scanning parameters that may be adjusted include scan clinical identifier (e.g., in a format Category.Identifier, such as Neuro.RoutineHead), bowtie filter setting, tube voltage mode (e.g., single energy or dual energy), tube current mode (e.g., manual (or fixed), or modulating), tube voltage selection assist mode (e.g., on or off), dual energy assist mode (e.g., on or off), helical pitch, cardiac acquisition phase, or contrast injection parameters. For example, contrast injection may be adjusted by adjusting one or more of volume, flow rate, or timing. Alternatively or additionally, the control information may adjust reconstruction parameters for reconstructing an image. For example, one or more of reconstruction kernel (or technique or algorithm for determining reconstruction kernel) or reconstruction thickness (or technique or algorithm for determining reconstruction thickness) may be adjusted. Additional examples of reconstruction parameters that may be adjusted include reconstruction clinical identifier (e.g., in a format Category.Identifier), cardiac phase location, motion correction algorithm on or off (and/or selection among different available motion correction algorithms), image enhancement filters, window width, window level, or noise reduction settings. Further examples of reconstruction parameters specific to a dual energy mode include tube voltage value, image type (e.g., monochromatic, material density pair, virtual unenhanced), metal artifact mode (e.g., metal artifact reduction on or off).

The depicted determination system 130 includes a processing unit 132 and a memory 134. The determination system 130 is shown as including a single processing unit 132; however, the block for the processing unit 132 may be understood as representing one or more processors that may be distributed or remote from each other (e.g., having multiple locations in a cloud or other distributed computing network system or arrangement represented by link 140). As discussed herein, the determination system may compare historical data correlating parameters, conditions, etc. for scans of a similar clinical context to determine if a protocol can be improved (e.g., to provide a better scan quality than determined for a protocol currently being analyzed). Data may be collected and stored for a number of different images along with evaluations to determine which settings work best for given condition, circumstance, or clinical task . . . can set forth protocol including assist features.

The processing unit 132 may include processing circuitry configured to perform one or more tasks, functions, or steps discussed herein. It may be noted that "processing unit" as used herein is not intended to necessarily be limited to a single processor or computer. For example, the processing unit 132 may include multiple processors and/or computers, which may be integrated in a common housing or unit, or which may distributed among various units or housings.

Generally, various aspects (e.g., programmed modules) of the processing unit 132 act individually or cooperatively with other aspects to perform one or more aspects of the methods, steps, or processes discussed herein (e.g., method 200 or aspects thereof). In the depicted embodiment, the memory 134 includes a tangible, non-transitory computer readable medium having stored thereon instructions for performing one or more aspects of the methods, steps, or processes discussed herein. In various embodiments, the memory 134 may include a database listing historical scan protocols and corresponding scan qualities used for comparison purposes to evaluate whether and/or how a currently analyzed scan protocol may be updated to improve performance. It may be noted other aspects of the system 100 (e.g., the reconstruction unit 120) may include similar processing units (e.g., including at least one processor and associated memory configured to act individually or cooperatively with other aspects to perform one or more aspects of the methods, steps, or processes discussed herein).

Figure 2:
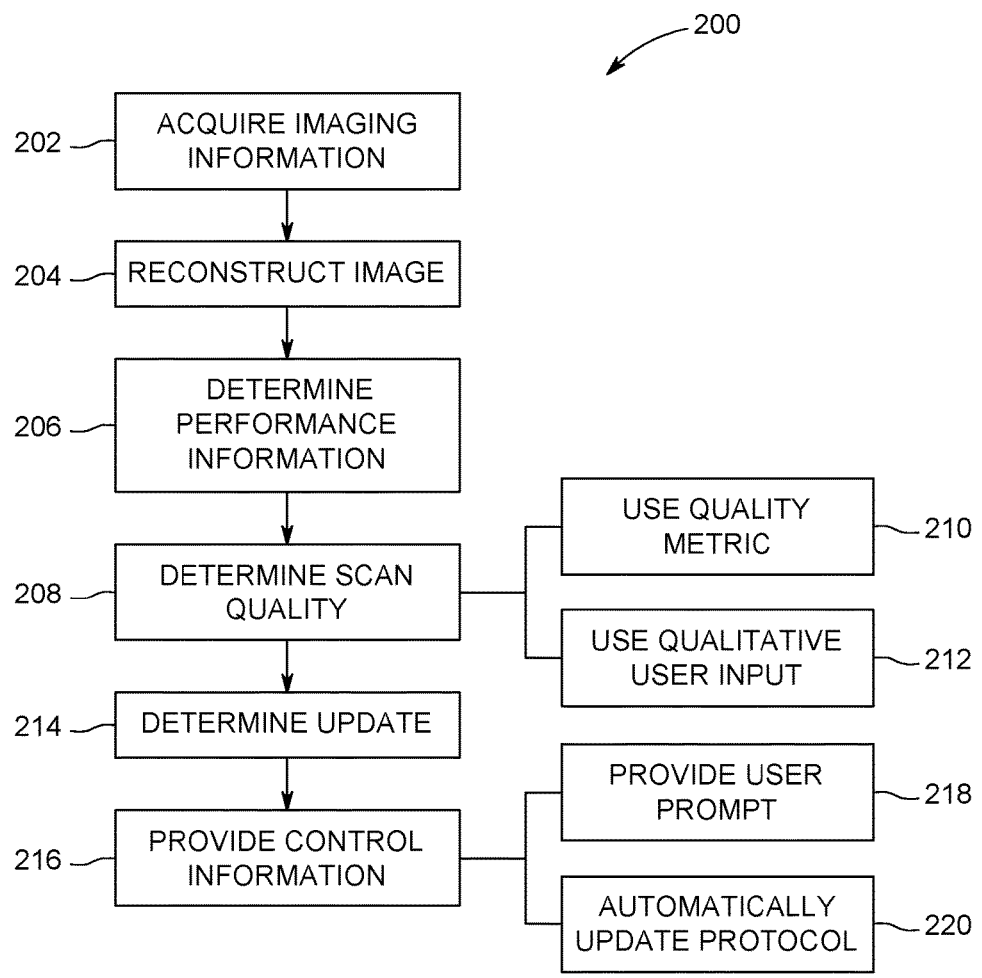
FIG. 2 is a flowchart of a method in accordance with various embodiments described herein.

FIG. 2 illustrates a flowchart of a method 200. The operations of FIG. 2 may be implemented by one or more processors executing program instructions stored in memory. The method 200, for example, may employ structures or aspects of various embodiments (e.g., systems and/or methods) discussed herein, such as the system 100. In various embodiments, certain steps (or operations) may be omitted or added, certain steps may be combined, certain steps may be performed simultaneously, certain steps may be performed concurrently, certain steps may be split into multiple steps, certain steps may be performed in a different order, or certain steps or series of steps may be re-performed in an iterative fashion. In various embodiments, portions, aspects, and/or variations of the method 200 may be used as one or more algorithms to direct hardware to perform one or more operations described herein. It should be noted, other methods may be used, in accordance with embodiments herein.

At 202, imaging information is acquired. For example, imaging information of a patient (or portion thereof) may be acquired using an imaging acquisition unit (e.g., imaging acquisition unit 110) pursuant to one or more protocols as discussed herein. For example, a particular clinical context or clinical task may have a particular corresponding specific protocol used in conjunction with the particular clinical context or clinical task. The imaging acquisition unit, for example, may be configured to acquire one or more of CT, PET, SPECT, MRI, or US imaging information.

At 204, an image is reconstructed with a reconstruction unit (e.g., reconstruction unit 120). In various embodiments, more than one image may be reconstructed. The image is reconstructed using the imaging information acquired at 202. Further, the image in various embodiments is reconstructed using a protocol. For example, a protocol for a given clinical context may specify both scanning parameters for acquiring information and reconstruction parameters for reconstructing an image using the acquired information. As discussed herein, such protocols may include or be associated with profiles or assist features.

At 206, performance information corresponding to the scan is determined (e.g., with a determination system such as determination system 130). The performance information in various embodiments may include usage information and/or imaging performance information. The usage information may include scan acquisition parameters, reconstruction parameters, or other machine settings (such as tube current, tube voltage, or the like), and may be used to identify, for example, user preferences or tendencies. The imaging performance information may correspond to the performance of the scan and/or the quality of one or more resulting images as discussed herein. The imaging performance information may include one or more of objective information (e.g., an IQ metric such as CNR, noise level, or the like), subjective information (e.g., a relative rating or grading provided by a user or operator), or a description of the scanning or reconstruction procedure (e.g., a note or comment on occurrences or observation by a user or operator, such as an observation of excessive motion of a subject being image or any other anomaly or abnormality during a procedure). Imaging performance information may be determined automatically (e.g., autonomously without user input) and/or using information input by a user.

At 208, a scan quality for the scan is determined based on the performance information (e.g. imaging performance information). For example, one or more image quality metrics and/or one or more user ratings or comments may be combined or otherwise used together to determine the scan quality. Additionally or alternatively, usage information corresponding to settings used to acquire the scan (and/or reconstruct an image) may be used to determine the scan quality. The scan quality may then be compared with scan qualities for previous scans for a similar clinical context or task.

In the depicted embodiment, at 210, a quality metric (or metrics) is automatically determined and used to determine the scan quality. At 212 of the illustrated embodiment, qualitative user input information is used to determine the scan quality. The automatically determine quality metric(s) may be used in conjunction with the user input information. For example, the user input information may be used to modify, confirm, or replace the automatically determined information.

At 214, an update is determined to a protocol. The update is performed based on or using the performance information acquired at 206, either directly or indirectly (e.g., using machine settings and/or a scan quality determined using imaging performance information). The update may be determined with a determination system such as determination system 130. The update in the depicted embodiment updates the protocol for a specific clinical context or task discussed in connection with steps 202 and/or 204. Historical information may be used to determine the update. For example, scan qualities for previously performed scans for a given clinical context or task may be collected and used to determine which parameter settings (or combination of settings) provide desired or relatively high scan quality. The scan qualities and corresponding protocols may be collected over a large number of scans to provide a robust base of knowledge. The historical information may be collected from a number of different users (e.g., different hospitals or hospital systems) to provide a wide range of information, and to allow improvements from one entity or institution to be used by others. For example, a scan quality for the scan performed at 202 may be compared to historically collected scan qualities to evaluate the performance of the protocol used at 202 and/or 204. To the extent the scan quality determined at 208 is less than desired or does not compare favorably to historical scans, the protocol may be updated. To the extent the scan quality determined at 208 compares favorably to historical scans, the protocol used at 202 and/or 204 (or values of one or more parameters of the protocol) may be stored and used to evaluate scans performed in the future.

At 216, control information is provided to implement the determined update. The determined update may be implemented to perform a scan or reconstruct an image for a subsequent procedure for the same clinical context or task as the scan performed at 202. Control information may be provided to at least one of the imaging acquisition unit used to acquire the imaging information at 202 or the reconstruction unit used to reconstruct the image at 204. The control information may be provided to the imaging acquisition unit to implement the determined update to perform a subsequent scan. For example, the control information may adjust one or more of tube voltage, tube current, focal spot size, collimation width, or rotational speed of a gantry. Additionally or alternatively, the control information may be provided to the reconstruction unit to implement the determined update to reconstruct a subsequent image. For example, the control information may adjust one or more of reconstruction kernel or reconstruction thickness. It may be noted that the control information may be provided to the imaging acquisition unit and/or reconstruction unit indirectly. For example, the control information updating the protocol may be sent to a remote processing unit (e.g., via link 140) which updates the protocol and subsequently transmits the updated protocol to the imaging acquisition unit and/or reconstruction unit.

It may be noted the control information may be implemented automatically in some embodiments, or with user intervention or involvement in some embodiments. For example, at 218, the control information includes a user prompt corresponding to the update of the protocol. For example, a user or operator (of either an acquisition unit or a reconstruction unit) may be provided with a prompt indicating the existence of an available update and/or details regarding which parameters will be updated as part of a protocol update. The user may then approve some or all of the provided update, disapprove some or all of the provided update, and/or modify some or all of the provided update. As another example, at 220, the control information is configured to automatically update the protocol (e.g., autonomously without user intervention).

Figure 3:
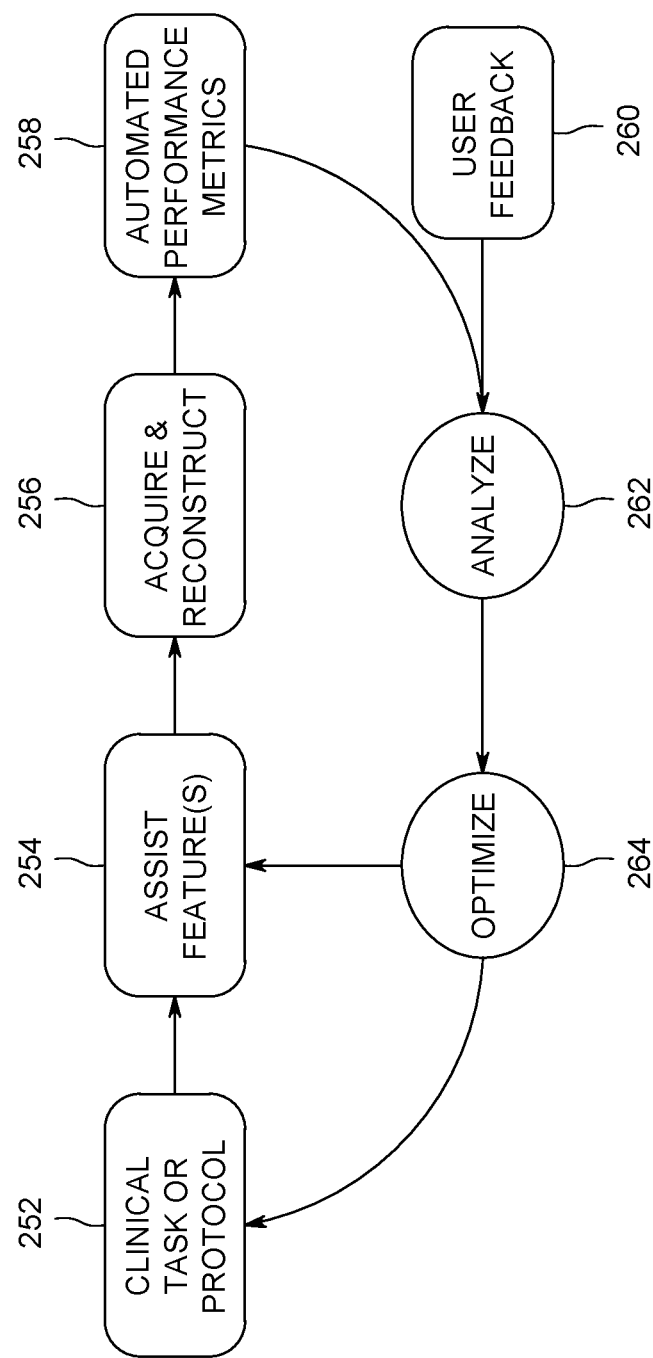
FIG. 3 is an example process flow diagram in accordance with various embodiments.

FIG. 3 is an example process flow 250 in accordance with various embodiments. The process flow 250 (and/or aspects thereof) may be utilized in conjunction with one or more embodiments discussed herein (e.g., one or more methods or systems, or aspects thereof, discussed herein). Generally, knowledge of the clinical task and associated CTQ's may be used to set scan acquisition and/or reconstruction parameters as part of a protocol at 252. Assist features as discussed herein may be employed at 254 to help tailor one or more aspects of the protocol for a particular patient or scan to be performed. Clinical task CTQ's may be used to customize the assist features.

At 256, imaging information is acquired and reconstructed. In the depicted embodiment, the imaging information is acquired using scan acquisition parameters from the protocol from 252 (which may be tailored by the assist features at 254), and the image is reconstructed using reconstruction parameters from the protocol from 252 (which may also be tailored by the assist features at 254). The reconstructed image is then provided to an automated analysis system and/or a human operator.

In the illustrated embodiment, at 258, automated performance metrics are generated (e.g., by determination system 130), and at 260, user feedback is provided (e.g., from a human operator viewing a displayed reconstructed image). In various embodiments, for a particular clinical use, the automated performance metrics and/or the user feedback may include one or more figures of merit quantifying quality of examination. For a given clinical task or identifier, corresponding figures of merit may be employed that provide objective qualifications of relative success (or lack thereof) of an imaging process. The particular figure(s) of merit may vary based on clinical use. For instance, one example figure of merit corresponds to the ability to freeze motion. Such a figure of merit may be utilized in connection with coronary artery scans, and in the selection or modification of phase acquisition parameters. In embodiments where both automated performance metrics and user feedback are utilized, the user rating may be compared to the performance metrics to one or more of modify or refine the automated metrics using the user ratings, evaluate the automated metrics using the user ratings, or evaluate the user (e.g., identifying user preferences based on the comparison of a user rating to an automated metric).

It may be noted that figures of merit may be patient specific or tailored for one or more patients having a particular characteristic. Further, thresholds or values of a given figure of merit may change based on one or more of clinical context, patient, or user preferences. For example, a patient or group of patients may be sensitive to iodine, so that a figure of merit for such a patient or group may quantify the amount of iodine with respect to image quality, as one example. Also, figures of merit may be tailored for users to accommodate user preferences. Patient characteristics and/or user preferences may affect a threshold, level, or target of a figure of merit defining what is configured "good," "successful," or the like. For example, a nominal contrast-to-noise ratio used in connection with a default figure of merit may have a value of "x." However, for an older patient who may not tolerate contrast as well as most patients, a value lower than x may be utilized. As another example, a threshold, level, or target may vary with patient size.

At 262 of the depicted embodiment, the automated performance metrics and user feedback are analyzed. At 264, the protocol specified previously at 254 (and/or assist features specified previously at 254) are optimized or otherwise modified or revised based on the analysis at 262. It may be noted that analysis and/or optimization may be performed during an active scan session, or at a later time. The analysis and/or optimization may be performed at a remote location. Generally, the user ratings and/or automated performance metrics may be used to modify the protocol and/or assist features to better satisfy or fulfill clinical CTQ's for a given clinical task. The modified or optimized protocol may then be used for subsequent scanning processes (and may be further modified or optimized based on automated performance metrics or user ratings for the subsequent scans).

Figure 4:
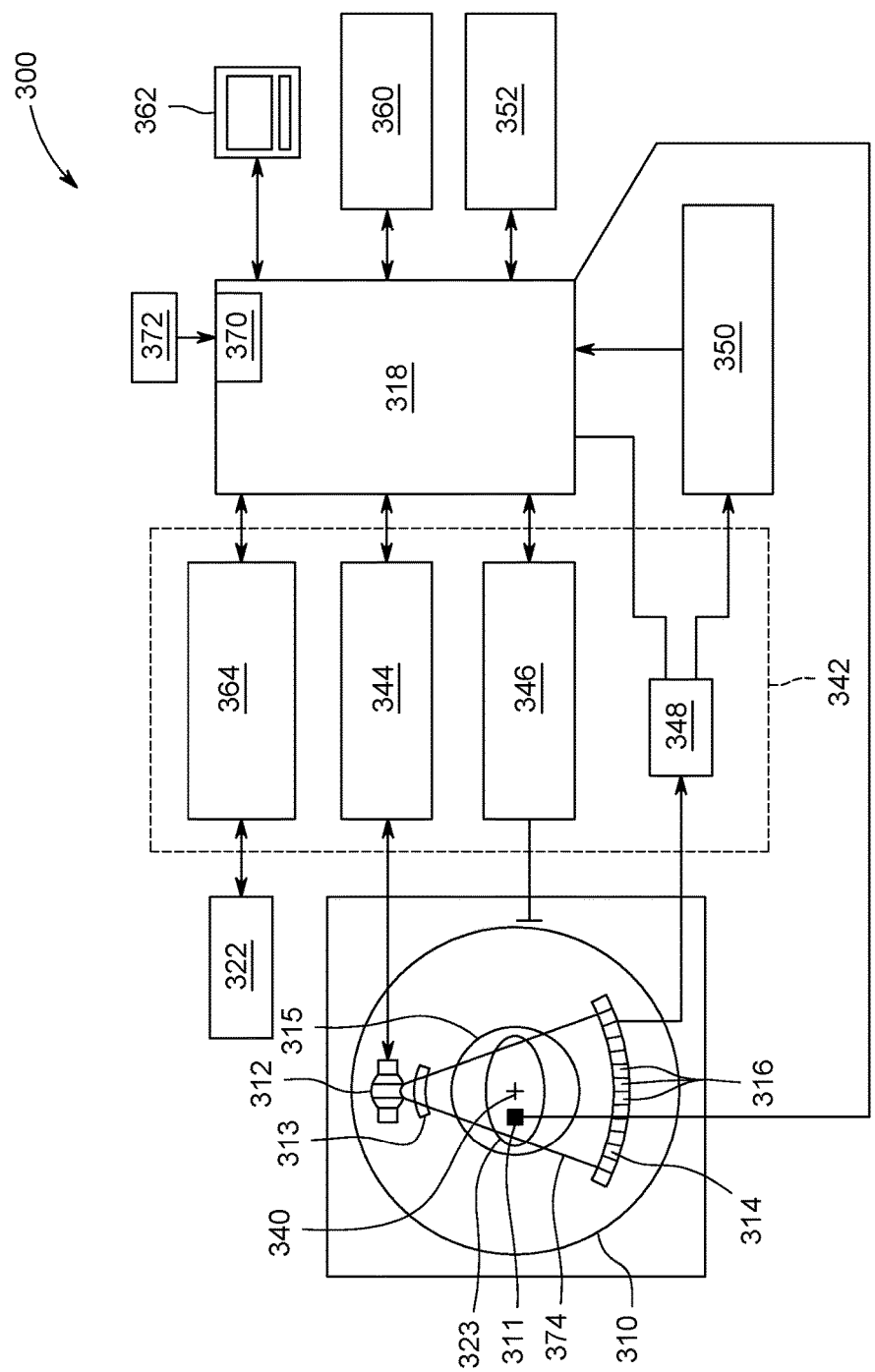
FIG. 4 is a schematic block diagram illustrating an imaging system in accordance with various embodiments described herein.

FIG. 4 illustrates a schematic diagram of an exemplary CT imaging system 300 that may be utilized to implement various embodiments discussed herein (e.g., as all or a portion of the acquisition unit 120). Although the CT imaging system 300 is illustrated as a standalone imaging system, it should be noted that the CT imaging system 300 may form part of a multi-modality imaging system in some embodiments. For example, the multi-modality imaging system may include the CT imaging system 300 and a positron emission tomography (PET) imaging system, or a single photon emission computed tomography (SPECT) imaging system. It should also be noted that in various embodiments one or more imaging modalities other than CT may be employed. It should also be understood that other imaging systems capable of performing the functions described herein are contemplated as being used.

The CT imaging system 300 includes a gantry 310 that has the X-ray source 312 that projects a beam of X-rays toward the detector array 314 on the opposite side of the gantry 310. A source collimator 313 and a bowtie filter module (not shown) are provided proximate the X-ray source 312. The detector array 314 includes a plurality of detector elements 316 that are arranged in rows and channels that together sense the projected X-rays that pass through a patient 323 (e.g., object of interest). The imaging system 300 may include a physiologic sensor 311 (e.g., electrocardiogram (ECG), a respiratory sensor) proximate to the patient 323 for cardiac or respiratory gating.

A motorized table 322 is utilized to move the patient 323 into and out of the gantry 310 at a table feed rate. Particularly, the table 322 moves at least a portion of the patient 323 through a gantry opening 315 along a z-axis that extends through the gantry 310. Further, the table 322 may be used to move the patient 323 vertically within the bore of the gantry 310.

The depicted detector array 314 includes a plurality of detector elements 316. Each detector element 316 produces an electrical signal, or output, that represents the intensity of an impinging X-ray beam and hence allows estimation of the attenuation of the beam as it passes through the patient 323. During a scan to acquire the X-ray projection data, the gantry 310 and the components mounted thereon rotate about a center of rotation 340. FIG. 4 shows only a single row of detector elements 316 (i.e., a detector row). However, the multi-slice detector array 314 includes a plurality of parallel detector rows of detector elements 316 such that projection data corresponding to a plurality of slices can be acquired simultaneously during a scan.

In the exemplary embodiment, the X-ray source 312 and the detector array 314 are rotated with the gantry 310 within the imaging plane and around the patient 323 to be imaged such that the angle at which an X-ray beam 374 intersects the patient 323 constantly changes. A group of X-ray attenuation measurements, i.e., projection data, from the detector array 314 at one gantry angle is referred to as a "view" or "projection." A "scan" of the patient 323 comprises a set of views made at different gantry angles, or view angles, during one or more revolutions of the X-ray source 312 and the detector array 314. In a CT scan, the projection data is processed to reconstruct an image that corresponds to a three-dimensional volume taken of the patient 323. It may be noted that, in some embodiments, an image may be reconstructed using less than a full revolution of data. For example, with a multi-source system, substantially less than a full rotation may be utilized. Thus, in some embodiments, a scan (or slab) corresponding to a 360 degree view may be obtained using less than a complete revolution.

Rotation of the gantry 310, the operation of the X-ray source 312, and position of the motorized table 322 are governed by an acquisition subsystem 342 based on one or more scan settings (e.g., tube current/voltage, focal spot size, duty cycle, kV pair, rotation speed, collimation width, field of view size, body dose, exposure time, head dose, helical pitch) defined by a scan prescription or protocol. The acquisition subsystem 342 includes an X-ray controller 344 that provides power and timing signals to the X-ray source 312 based on the scan settings defined by the scan prescription or protocol. The X-ray controller 344 may deliver power (e.g., tube current, tube voltage) and/or configure the X-ray source 312 to project X-rays having a certain field of view and/or collimation width (e.g., collimation slab) based on the scan settings defined by the scan prescription or protocol. Additionally or alternatively, the X-ray controller 344 may control a focal spot size of the X-ray source 312 based on the scan settings defined by the scan prescription or protocol. Optionally, for dual-energy CT scans, the X-ray controller 344 may define the dual energy levels (e.g., kV pair) and duty cycle of the X-rays emitted by the X-ray source 312.

The acquisition subsystem 342 also includes a gantry motor controller 346 that controls the rotational speed and position of the gantry 310. For example, the gantry motor controller 346 may rotate the gantry 310 at a rotational velocity based on the scan settings defined by the scan prescription or protocol.

In addition, the acquisition subsystem 142 may also include a table motor controller 164 that controls the motorized table 322 to position the patient 323 in the gantry 310 based on the scan settings defined by the scan prescription or protocol. Particularly, the motorized table 322 moves at least a portion of the patient 323 through the gantry opening at a table feed rate.

The scan prescription or protocol may be stored on a storage device 352 which is communicatively coupled to the acquisition subsystem 342. The storage device 352 may be a tangible and non-transitory computer readable medium such as flash memory, RAM, ROM, EEPROM, and/or the like. The scan prescription or protocol may be defined by a processing unit 318.

The processing unit 318 may include one or more processors. Optionally, the processing unit 318 may include a central controller circuit (CPU), one or more microprocessors, a graphics controller circuit (GPU), or any other electronic component capable of processing inputted data according to specific logical instructions. Additionally or alternatively, the processing unit 318 may execute instructions stored on a tangible and non-transitory computer readable medium (e.g., the storage device 352, integrated memory of the processing unit 318). The processing unit 318 receives the projection data from the detector array 314 and processes the projection data to reconstruct an image of the patient 323.

The processing unit 318 is operably coupled to a display 362 and the user interface 360. The display 362 may include one or more liquid crystal displays (e.g., light emitting diode (LED) backlight), organic light emitting diode (OLED) displays, plasma displays, CRT displays, and/or the like. The display 162 allows the operator to observe the reconstructed image and other data generated by the processing unit 318. For example, the display 362 may display patient information, one or more CT images, components of a display interface, measurements, diagnosis, treatment information, and/or the like.

The user interface 360 controls operations of the CT imaging system 300 and is configured to receive inputs (e.g., CID) from the user. The user interface 360 may include a keyboard, a mouse, a touchpad, one or more physical buttons, and/or the like. Optionally, the display 362 may be a touch screen display, which includes at least a portion of the user interface 342. For example, the user may select one or more user selectable elements shown on the display by touching or making contact with touch sensitive portions of the display 362.

A data acquisition system (DAS) 348 in the acquisition subsystem 342 samples analog data from detector elements 316 and converts the data to digital signals, the projection data, for subsequent processing. An image reconstructor circuit 350 receives the projection data from the DAS 348 and performs an image reconstruction. The image reconstructor circuit 350 may include one or more processors, field programmable arrays, one or more ASICs, a CPU, or any other electronic component capable of processing inputted data according to specific logical instructions. Additionally or alternatively, the image reconstructor circuit 350 may execute programmed instructions stored on a tangible and non-transitory computer readable medium (e.g., the storage device 352, integrated memory of the image reconstructor circuit 350). For example, the one or more processors may perform one or more operations by executing programmed instructions stored on the storage device 352 and/or integrated memory such as EEPROM. The image reconstructor circuit 350 may generate the resultant medical image based on reconstructed settings received via the user interface 360 and/or based on the scan attributes. The reconstruction settings may include select keV energy level(s), iterative reconstruction (e.g., adaptive statistical reconstruction), direct multi-planar reconstruction, algorithmic reconstruction, and/or the like.

The projection data is processed by the image reconstructor circuit 350 to reconstruct resultant medical images that corresponds to a two dimensional (2D) slice taken through the patient 323. The image reconstructor circuit 350 may convert the attenuation measurements associated with the projection data into a medical image of the patient 323. The attenuation measurements are typically converted into units of "CT numbers" or Hounsfield units (HU). The image is represented as a matrix of numbers, with each individual number in the image matrix representing a three-dimensional (3D) volume element in the scanned part, called a "voxel." To obtain a visual image, each voxel is represented as a 2D picture element, or "pixel." Each pixel has a shade of gray based on the HU value representing the attenuation measurement within the corresponding voxel. For example, the HU value may correspond to a brightness of each pixel such that a pixel having a higher HU value may be brighter relative to a pixel having a lower HU value. The reconstructed medical images generated by the image reconstructor circuit 350 are input to the processing unit 318 that stores the image in the storage device 352. Optionally, the image reconstructor circuit 350 may be integrated with and/or similar operations may be performed by the processing unit 318.

Additionally or alternatively, the processing unit 318 includes a device 370, for example, a CD-ROM drive, DVD drive, magnetic optical disk (MOD) device, and/or any other digital device including a network connecting device such as an Ethernet device for reading instructions and/or data from a tangible non-transitory computer-readable medium 372.

It should be noted that the various embodiments may be implemented in hardware, software or a combination thereof. The various embodiments and/or components, for example, the modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a solid-state drive, optical disk drive, and the like. The storage device may also be other similar means for loading computer programs or other instructions into the computer or processor.

As used herein, the term "computer," "processing unit," "subsystem" or "module" may include any processor-based or microprocessor-based system including systems using microcontrollers, reduced instruction set computers (RISC), ASICs, logic circuits, and any other circuit or processor capable of executing the functions described herein. The above examples are exemplary only, and are thus not intended to limit in any way the definition and/or meaning of the term "computer".

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments. The set of instructions may be in the form of a software program. The software may be in various forms such as system software or application software and which may be embodied as a tangible and non-transitory computer readable medium. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, a structure, limitation, or element that is "configured to" perform a task or operation is particularly structurally formed, constructed, or adapted in a manner corresponding to the task or operation. For purposes of clarity and the avoidance of doubt, an object that is merely capable of being modified to perform the task or operation is not "configured to" perform the task or operation as used herein. Instead, the use of "configured to" as used herein denotes structural adaptations or characteristics, and denotes structural requirements of any structure, limitation, or element that is described as being "configured to" perform the task or operation. For example, a processing unit, processor, or computer that is "configured to" perform a task or operation may be understood as being particularly structured to perform the task or operation (e.g., having one or more programs or instructions stored thereon or used in conjunction therewith tailored or intended to perform the task or operation, and/or having an arrangement of processing circuitry tailored or intended to perform the task or operation). For the purposes of clarity and the avoidance of doubt, a general purpose computer (which may become "configured to" perform the task or operation if appropriately programmed) is not "configured to" perform a task or operation unless or until specifically programmed or structurally modified to perform the task or operation.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments without departing from their scope. While the dimensions and types of materials described herein are intended to define the parameters of the various embodiments, they are by no means limiting and are merely exemplary. Many other embodiments will be apparent to those of skill in the art upon reviewing the above description. The scope of the various embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f) unless and until such claim limitations expressly use the phrase "means for" followed by a statement of function void of further structure.

This written description uses examples to disclose the various embodiments, including the best mode, and also to enable any person skilled in the art to practice the various embodiments, including making and using any devices or systems and performing any incorporated methods. The patentable scope of the various embodiments is defined by the claims, and may include other examples that occur to those skilled in the art. Such other examples are intended to be within the scope of the claims if the examples have structural elements that do not differ from the literal language of the claims, or the examples include equivalent structural elements with insubstantial differences from the literal language of the claims.

What is claimed is:
1. A system comprising:
an imaging acquisition unit that performs a scan to acquire imaging information of a current patient, wherein the scan is performed using a protocol that is used for multiple patients, wherein the protocol includes a general portion configured for a particular clinical task and a profile portion tailored for the current patient, the imaging acquisition unit including an X-ray source and a computed tomography (CT) detector;
a reconstruction unit that reconstructs an image using the imaging information using the protocol, the reconstruction unit including at least one reconstruction processor configured to reconstruct the image;
a determination system communicatively coupled to the imaging acquisition unit and the reconstruction unit, the determination system comprising at least one processor configured to:
acquire performance information corresponding to the scan;
determine a scan quality for the scan based on the performance information and the image reconstructed using the protocol;
determine an update to the protocol based on the scan quality for use in a subsequent procedure; and
provide control information to at least one of the imaging acquisition unit or the reconstruction unit to implement the determined update to the protocol for at least one of performing a subsequent scan for a subsequent patient that is different from the current patient, or reconstructing a subsequent image for the subsequent patient that is different from the current patient.

2. The system of claim 1, wherein the control information comprises a user prompt corresponding to the update of the protocol used to at least one of acquire the imaging information or reconstruct the image.

3. The system of claim 1, wherein the control information comprises an automatic update of the protocol used to at least one of acquire the imaging information or reconstruct the image.

4. The system of claim 1, wherein the control information adjusts one or more of a tube voltage, tube current, focal spot size, collimation width, rotational speed of a gantry, scan clinical identifier, bowtie filter setting, tube voltage mode, tube current mode, helical pitch, cardiac acquisition phase, or contrast injection.

5. The system of claim 1, wherein the control information adjusts one or more of a reconstruction kernel, a reconstruction thickness, a reconstruction clinical identifier, a cardiac phase location, a motion correction algorithm, an image enhancement filter, a window width, or a window level.

6. The system of claim 1, wherein the performance information comprises imaging performance information corresponding to the image, and wherein the scan quality is determined based on the imaging performance information.

7. The system of claim 6, wherein the imaging performance information includes at least one of an automatically determined quality metric or qualitative user input information based on the image reconstructed using the protocol.

8. The system of claim 1, wherein the determination system is configured to determine at least one figure of merit quantifying quality of examination based on the image reconstructed using the protocol, and use the figure of merit to determine the update to the protocol.

9. A method comprising:
acquiring imaging information of a current patient via with an imaging acquisition unit during a scan, wherein the scan is performed using a protocol that is used for multiple patients, wherein the protocol includes a general portion configured for a particular clinical task and a profile portion tailored for the current patient, the imaging acquisition unit including an X-ray source and computed tomography (CT) detector;
reconstructing, with a reconstruction unit that includes at least one reconstruction processor, using the protocol, an image using the imaging information acquired during the scan;
determining, with at least one processor, performance information corresponding to the scan;
determining, with the at least one processor, a scan quality for the scan based on the performance information and the image reconstructed using the protocol;
determining, with the at least one processor, an update to the protocol based on the scan quality for use in a subsequent procedure; and
providing control information to at least one of the imaging acquisition unit or the reconstruction unit to implement the determined update to the protocol for at least one of performing a subsequent scan for a subsequent patient that is different from the current patient, or reconstructing a subsequent image for the subsequent patient that is different from the current patient.

10. The method of claim 9, wherein providing the control information comprises providing a user prompt corresponding to the update of the protocol.

11. The method of claim 9, wherein providing the control information comprises automatically updating the protocol.

12. The method of claim 9, wherein providing the control information comprises adjusting one or more of a tube voltage, tube current, focal spot size, collimation width, rotational speed of a gantry, scan clinical identifier, bowtie filter setting, tube voltage mode, tube current mode, helical pitch, cardiac acquisition phase, or contrast injection.

13. The method of claim 9, wherein the providing the control information comprises adjusting one or more of a reconstruction kernel, a reconstruction thickness, a reconstruction clinical identifier, a cardiac phase location, a motion correction algorithm, an image enhancement filter, a window width, or a window level.

14. The method of claim 9, wherein the performance information comprises imaging performance information corresponding to the image, and wherein the scan quality is determined based on the imaging performance information.

15. The method of claim 9, wherein determining the scan quality comprises using at least one of an automatically determined quality metric or qualitative user input information based on the image reconstructed using the protocol.

16. The method of claim 9, wherein determining the scan quality comprises determining at least one figure of merit quantifying quality of examination based on the image reconstructed using the protocol.

17. A tangible and non-transitory computer readable medium comprising one or more computer software modules configured to direct one or more processors to:
perform a scan to acquire imaging information of a current patient, wherein the scan is performed using a protocol that is used for multiple patients, wherein the protocol includes a general portion configured for a particular clinical task and a profile portion tailored for the current patient;
reconstruct an image under the protocol using the imaging information;
determine performance information corresponding to a scan;
determine a scan quality for the scan based on the performance information and the image reconstructed under the protocol;
determine an update to the protocol based on the scan quality for use in a subsequent procedure; and provide control information to at least one of an imaging acquisition unit or a reconstruction unit to implement the determined update to the protocol for at least one of performing a subsequent scan for a subsequent patient that is different from the current patient, or reconstructing a subsequent image for the subsequent patient that is different from the current patient.

18. The tangible and non-transitory computer readable medium of claim 17, wherein the one or more computer software modules are further configured to direct the one or more processors to automatically update the protocol.

19. The tangible and non-transitory computer readable medium of claim 17, wherein the performance information comprises imaging performance information corresponding to the image reconstructed using information acquired during the scan, and wherein the scan quality is determined based on the imaging performance information.

20. The tangible and non-transitory computer readable medium of claim 17, wherein the one or more computer software modules are further configured to direct the one or more processors to determine the scan quality using at least one of an automatically determined quality metric or qualitative user input information based on the image reconstructed under the protocol.

\* \* \* \* \*